(12) United States Patent
Togawa et al.

(10) Patent No.: US 6,252,658 B1
(45) Date of Patent: Jun. 26, 2001

(54) PARTICLE SIZE DISTRIBUTION MEASURING APPARATUS

(75) Inventors: Yoshiaki Togawa; Tatsuo Igushi; Toshiya Ito; Yukio Sakai, all of Miyanohigashi-machi (JP)

(73) Assignee: Horiba, Ltd., Kyoto (JP)

( * ) Notice: Subject to any disclaimer, the term of this patent is extended or adjusted under 35 U.S.C. 154(b) by 0 days.

(21) Appl. No.: 09/415,152

(22) Filed: Oct. 8, 1999

(30) Foreign Application Priority Data

Oct. 16, 1998 (JP) .................................................. 10-294333

(51) Int. Cl.[7] .................................................... G01N 15/02
(52) U.S. Cl. ........................... 356/335; 356/336; 356/337
(58) Field of Search .................................... 356/335, 336, 356/337, 338, 339, 342; 250/575, 574

(56) References Cited

U.S. PATENT DOCUMENTS

| | | | |
|---|---|---|---|
| 4,953,978 | * | 9/1990 | Bott et al. .............................. 356/366 |
| 4,957,363 | * | 9/1990 | Takeda et al. ......................... 356/343 |
| 5,135,306 | * | 8/1992 | Kanebako et al. .................... 356/336 |
| 5,185,641 | * | 2/1993 | Igushi et al. .......................... 356/343 |
| 5,400,139 | * | 3/1995 | Shimaoka .............................. 356/336 |
| 5,506,673 | * | 4/1996 | Kosaka et al. ........................ 356/366 |
| 5,737,078 | | 4/1998 | Takarada et al. . |
| 5,796,480 | | 8/1998 | Igushi . |

FOREIGN PATENT DOCUMENTS

| | | | |
|---|---|---|---|
| 02193041 | * | 7/1990 | (JP) ...................................... 356/366 |
| 403115950 | * | 5/1991 | (JP) ...................................... 356/336 |
| 643950 | | 6/1994 | (JP) . |

* cited by examiner

Primary Examiner—Frank G. Font
Assistant Examiner—Sang H. Nguyen
(74) Attorney, Agent, or Firm—Price and Gess

(57) ABSTRACT

A particle size distribution measuring apparatus includes a source of laser light for providing a laser beam to a sample cell that can hold a sample to be measured. A condenser lens converges the laser beam towards the sample cell along an optical axis. The position on the other side of the sample cell is a ring detector unit that can be aligned with the optical axis to measure light intensity at relatively small scattering angles from contact with particles in the sample cell. An array of detectors can be operatively positioned on a substrate with appropriate amplifying multiplying and analog to digital conversion capacity for measuring light intensity at relatively large scatter angles. The outputs of the ring detector unit and the array of detectors can be used to determine the particle size distribution of particles in the sample.

17 Claims, 4 Drawing Sheets

PARTICLE SIZE DISTRIBUTION MEASURING APPARATUS

BACKGROUND OF THE INVENTION

1. Field of the Invention

The present invention relates to a particle size distribution measuring apparatus which detects a diffraction/scattering light generated by irradiating a laser beam onto a dispersing particle group, and measures a particle (grain) size distribution of the particle group on the basis of an intensity signal of the scattered light obtained by the detection.

2. Description of Related Art

In a particle size distribution measuring apparatus using a diffraction or scattering phenomenon of light by particles, an intensity distribution of diffraction light or scattering light, that is, a relationship between a diffraction or scattering angle and a light intensity is measured, and then, this measured result is subjected to operational processing based on a Fraunhofer diffraction theory or Mie scattering theory, and thereby, a particle size distribution of a sample particle is calculated (computed). The aforesaid particle size distribution measuring apparatus has been used for research and development of raw materials in a mining industrial field such as the cement or ceramic industry, and in ceramics, in particular.

In the development of new materials in the ceramic and polymer fields, a demand has been recently made to measure micro particles in a sub-micron region, and therefore, efforts have been made to develop instruments which can measure not only relatively large particles, but also particles in a sub-micron region.

An example of a particle size distribution measuring apparatus is disclosed in Japanese Examined Patent Publication (Kokoku) No. 6-43950. FIG. 4 is a view schematically showing a construction of the particle size distribution measuring apparatus disclosed in the above publication. In FIG. 4, a reference numeral 41 denotes a sample cell comprising a transparent container which contains a liquid (hereinafter, referred to as a sample solution) 42 prepared by dispersing a particle group of a target specimen for measurement in a medium liquid. A laser beam source 43 which is located on one side (rear side) of the cell 41 provides an enlarged parallel laser beam 44 from a beam expander (not shown) so as to irradiate the cell 41.

A collective (condenser) lens 45 is located on the other side (front side) of the cell 41, and a ring detector 46 is arranged on a focal position of the collective lens 41. The ring detector 46 is constructed in such a manner that a plurality of photo-sensors having a ring or semi-ring like light receiving surface having mutually different radius are coaxially arranged around an optical axis of the collective lens 45. Further, the ring detector 46 receives light scattered/diffracted at a relatively small angle off of the optical axis of the laser beam 44 which has been diffracted or scattered by the particles in the cell 41 for each scattering angle, and then, measures each respective light intensity.

An optical detector group 47 for wide-angle scattering light detects each light scattered/diffracted at a relatively large angle of the laser beam 44 which has been diffracted or scattered by the particles in the cell 41 for each scattering angle. Further, the optical detector group 47 for wide-angle scattering light is composed of the collective lens 45 and a plurality of photo-sensors 48 to 53 which are located at an angle different from the ring detector 46, and can detect a wide-angle scattering light which exceeds a predetermined angle by particles in the cell 41, in accordance with each located angle. More specifically, the photo-sensors 48 to 51 detect a forward scattering light, the photo-sensor 52 detects a side scattering light, and the photo-sensor 53 detects a backward scattering light.

A reference numeral 54 denotes a pre-amplifier for amplifying an output of the photo-sensors constituting the above ring detector 46, reference numerals 55 to 58 individually denote pre-amplifiers for amplifying each output of the photo-sensors 48 to 51 for forward scattering light, and reference numerals 59 and 60 individually denote pre-amplifiers for output of the photo-sensor 52 for side scattering light and the photo-sensor 53 for backward scattering light. A multiplexor 61 successively captures each output of the pre-amplifiers 54 to 60, and successively transmits the output to an A/D converter 62, and a computer 63 functions as a processor to which an output of the A/D converter 62 is inputted.

The computer 63 stores a program for processing the outputs converted into a digital signal (the digital data relative to light intensity) of the ring detector 46 and photo-sensor 48 to 53 on the basis of a known Fraunhofer diffraction theory or Mie scattering theory and determining a particle size distribution of the particle group.

In the aforesaid particle size distribution measuring apparatus, when sample liquid 42 is contained in the cell 41, the laser beam 44 is irradiated on the sample cell 41 from the laser beam source 43 and the laser beam 44 is diffracted or scattered by particles contained in the cell 41. Of the diffraction light or the scattering light, a light having a relatively small scattering angle is imaged on the ring detector 46 by means of the collective lens 45. In this case, the photo-sensor arranged on the outer peripheral side of the ring detector 46 receives a light having a larger scattering angle while the photo-sensor arranged on an inner peripheral side thereof receives light having a smaller scattering angle. Thus, a light intensity detected by the outer peripheral side photo-sensor reflects a particle quantity having a smaller particle size, and a light intensity detected by the inner peripheral side photo-sensor reflects a quantity of sample particle having a larger particle size. The light intensity detected by each photo-sensor is converted into an analog electric signal, and further, is inputted to the multiplexor 61 via the pre-amplifier 54.

On the other hand, of the laser beam 44 diffracted or scattered by the particles, a relatively large scattering angle light, which is not converged by the collective lens 45, is detected by means of the photo-sensors 48 to 53, and then, the light intensity distribution is measured. In this case, the photo-sensors 48 to 51 for forward scattering light, the photo-sensor 52 for side scattering light and the photo-sensor 53 for backward scattering light, successively detect scattering light from a particle having a small particle (grain) size. A light intensity detected by each of these photo-sensors 48 to 53 is converted into an analog electric signal, and then, is inputted to the multiplexor 61 via pre-amplifiers 55 to 60.

In the multiplexor 61, measurement data from the ring detector 46 and photo-sensors 48 to 53, that is, the analog electric signal is successively captured in a predetermined order. Then, the analog electric signal captured by the multiplexor 61 is made into a serial signal, and is successively converted into a digital signal by means of the A/D converter 62, and further, is inputted to the computer 63. The computer 63 processes light intensity data for each scattering angle obtained by each of the ring detector 46 and the photo-sensors 48 to 53 on the basis of a Fraunhofer diffraction theory and a Mie scattering theory.

As seen from the above description, in such a particle size distribution measuring apparatus, the light intensity distribution of the scattering light having a large particle size range is measured by means of the ring detector 46 while the light intensity distribution of the wide-angle scattering light having a small particle size range is measured by means of the photo-sensors 48 to 53. Then, the outputs of these ring detector 46 and photo-sensors 48 to 53 are processed by means of the computer 63, so that a particle size distribution of a particle group can be determined over a wide range from a relatively large particle size to a micro particle size.

However, the aforesaid particle size distribution measuring apparatus has the following problem. More specifically, in the particle size distribution measuring apparatus, a parallel beam is used as the laser beam 44 for irradiating the particle group contained in the cell 41; therefore, light having a small scattering angle is generated by particles having a relatively large particle size and the light is converged on the ring detector 46. For this reason, the collective lens 45 must be interposed between the cell 41 and the ring detector 46. As a result, this arrangement requires a long optical path length from the laser beam source 43 to the ring detector 46.

Moreover, the aforesaid arrangement of the collective lens 45 is a factor in causing the following problem. More specifically, in order to detect scattering light from a smaller particle (light having a large scattering angle), a plurality of photo-sensors 48 to 53 must be located so as to constitute the optical detector group 47 for wide-angle scattering light. In order to make the wide-angle scattering light incident upon these photo-sensors 48 to 53, there is a requirement of an accurate positional relationship between the collective lens 45 and the photo-sensors 48 to 53, in particular, the photo-sensors 48 to 51 for forward scattering light. Thus, in the aforesaid conventional particle size distribution measuring apparatus, an arrangement space must be widened so that the scattering light from the cell 41 can be securely incident upon all of photo-sensors 48 to 53.

As is evident from the above description, in the conventional particle size distribution measuring apparatus, the parallel laser beam 44 is irradiated on the cell 41, and the collective lens 45 is interposed between the cell 41 and the ring detector 46 and for this reason the apparatus must be made into a large size.

U.S. Pat. No. 5,737,078 discloses a flow cell for a cytoanalyzer and U.S. Pat. No. 5,796,480 is cited of interest.

The prior art is still seeking to provide an economical and compact portable measuring apparatus.

SUMMARY OF THE INVENTION

The present invention has been made taking the aforesaid problems in the prior art into consideration. It is, therefore, an object of the present invention to provide a small and compact particle size distribution measuring apparatus which can securely measure a particle size distribution of particles over a wide range from a micro particle size to a large particle size.

To achieve the above object, the present invention provides a particle size distribution measuring apparatus which is constructed in such a manner that diffracted/scattered light generated by irradiating a laser beam from a laser light source on a particle group dispersed in a sample cell, a light intensity of a laser beam having a small scattering angle is detected by means of a ring detector for each scattering angle. The ring detector includes a plurality of concentric channels of photo detective material. A light intensity of a laser beam having a large scattering angle of the diffracted/scattered light is detected by means of a plurality of photo-sensors formed into an array, and thus, a particle size distribution of the particle group is measured on the basis of a scattering light intensity signal from the ring detector and the photo-sensors with a collective lens being interposed between the laser light source and the cell so that a laser beam converged by the condenser lens is irradiated on the particle group.

In the aforesaid particle size distribution measuring apparatus, the collective lens is interposed between the laser light source and the cell, and the laser beam is converged by the condenser lens to irradiated the particle group. It is possible to collect light having a small scattering angle generated by the particles having a relatively large particle size onto the ring detector without interposing the condenser lens between the cell and the ring detector. Further, it is possible to make a shorter optical path length from the laser beam source to the ring detector as compared with the case where the parallel beam is irradiated to the particle group in the sample cell. Furthermore, the condenser lens is not interposed between the cell and the ring detector; therefore, it is possible to sufficiently secure an optical path of the scattering light from cell, and to arbitrarily arrange photo-sensors on a position equivalent to respective scattering angles. Therefore, the construction of the particle size distribution measuring apparatus can be simplified and a small-size and compact particle size distribution measuring apparatus can be obtained.

In the aforesaid particle size distribution measuring apparatus, the plurality of photo-sensors may be individually located on a substrate such as an electric circuit board, and these photo-sensors may be collectively located on a single electric circuit board.

BRIEF DESCRIPTION OF THE DRAWINGS

The general purpose of this invention, as well as a preferred mode of use, its objects and advantages will best be understood by reference to the following detailed description of an illustrative embodiment with reference to the accompanying drawings in which like reference numerals designate like parts throughout the figures thereof, and wherein.

DETAILED DESCRIPTION OF THE PREFERRED EMBODIMENTS

The following description is provided to enable any person skilled in the art to make and use the invention and sets forth the best modes contemplated by the inventors of carrying out their invention. Various modifications, however, will remain readily apparent to those skilled in the art, since the general principles of the present invention have been defined herein specifically to provide a compact particle size distribution measuring apparatus with a unitary substrate for supporting an array of photo detector and associated circuitry.

In the Figures, like elements will have the same reference numbers.

Figure 1:
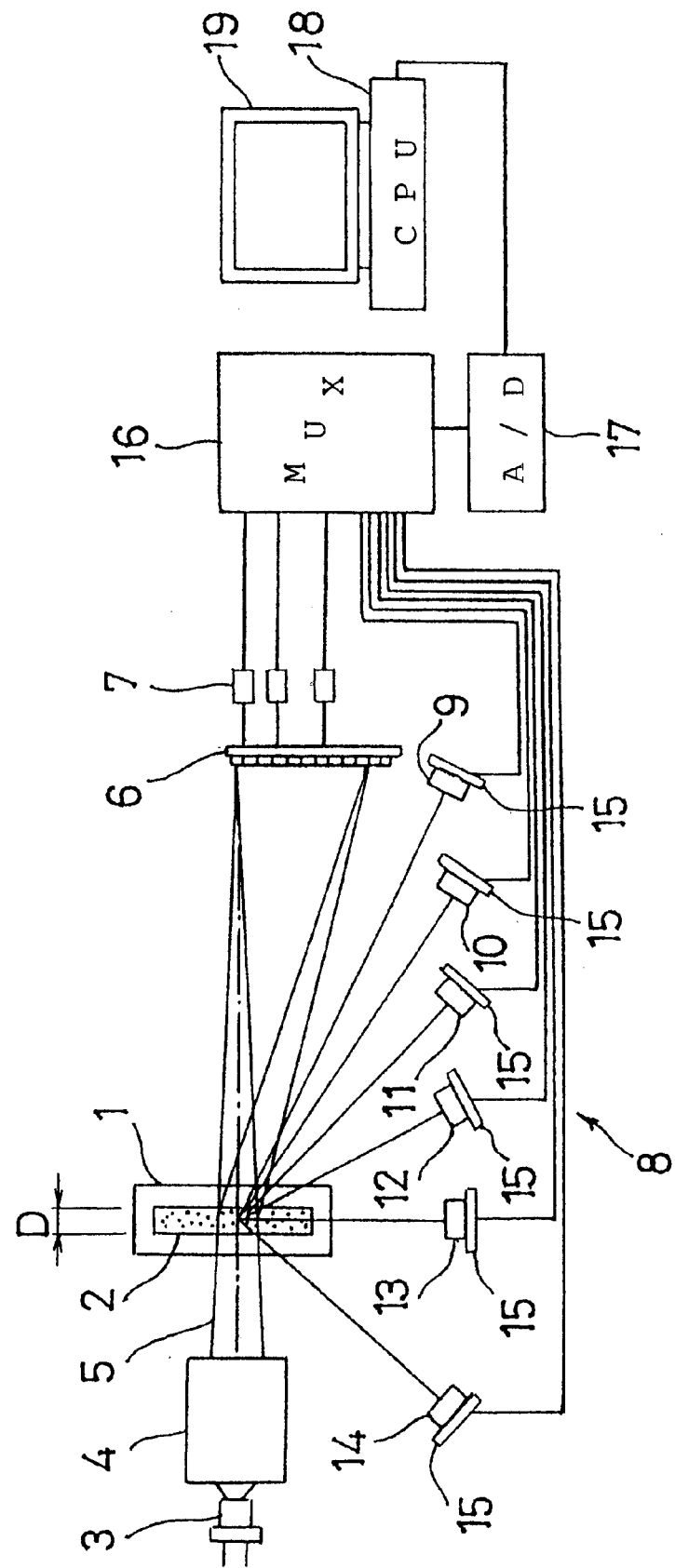
FIG. 1 is a view schematically showing a construction of a particle size distribution measuring apparatus according to a first embodiment of the present invention.

FIG. 1 schematically shows a construction of a particle size distribution measuring apparatus according to one embodiment of the present invention. In FIG. 1, a reference numeral 1 denotes a cell comprising a transparent container which contains a liquid, thereinafter, referred to as a sample solution 2 prepared by dispersing a particle group of a target for measurement in a medium liquid. An optical path direction length or optical path length D is set shorter than that generally set in a type of conventional apparatus. A laser beam or light source 3, which is located on one side of a rear side of the cell 1 emits parallel laser light. A condenser or collective lens 4 is interposed between the laser light source 3 and the cell 1. A laser light or laser beam emitted from the laser light source 3 is made into a converged light hereinafter, referred to as a converged laser beam 5 so as to irradiate the sample solution 2 in the cell 1.

A ring detector 6 is located on the other side or front side of the cell 1, and is arranged at a position where the converged laser beam 5, transmitted through the cell, 1 is focused. The ring detector 6 may be constructed in such a manner that a plurality of photo-sensors having a ring, semi-ring or quarter-ring light receiving surface or channel having mutually different radius are coaxially arranged around an optical axis of the condenser lens 4. Further, the ring detector 6 receives a light scattered/diffracted at a relatively small angle of the converged laser beam 5 diffracted or scattered by the particles in the cell 1 for each scattering angle, and then, measures each light intensity. Consequently, there is no necessity to use a lens for converging the scattered laser beam on the other side of the cell 1 from the laser light source 3. An example of a possible ring detector is shown in U.S. Pat. No. 5,936,729 which is incorporated herein by reference. A pre-amplifier 7 amplifies each output of the photo-sensors constituting the ring detector 6.

Moreover, an optical detector group 8 for measuring wide-angle scattering light is located in the vicinity of the cell 1. The optical detector group 8 for wide-angle scattering light detects each light scattered/diffracted at a relatively large angle of the converged laser beam 5 diffracted or scattered by the particles in the cell 1 for each scattering angle. Further, the optical detector group 8 for wide-angle scattering light is composed of a plurality of photo-sensors 9 to 14 which are located at an angle different from the ring detector 6, and can detect a predetermined angle of scattering light which exceeds a predetermined angle by particles in the cell 1, in accordance with each located angle. More specifically, the photo-sensors 9 to 12 detect a forward scattering light, the photo-sensor 13 detects a side scattering light, and the photo-sensor 14 detects a backward scattering light. A reference numeral 15 collectively denotes a substrate such as an electric circuit board which holds each of photo-sensors 9 to 14 at a predetermined angle and includes a pre-amplifier.

A reference numeral 16 denotes a multiplexor which successively captures each output of the pre-amplifier 7 of the electric circuit board 15, and then, successively transmits the output to an A/D converter 17. A computer 18 functions as a processor to which an output of the A/D converter 17 is inputted. The computer 18 stores a program for processing the outputs converted into a digital signal (the digital data relative to light intensity) of the ring detector 6 and photo-sensors 9 to 14 on the basis of a Fraunhofer diffraction theory or Mie scattering theory and determining a particle size distribution of the particle group. A color display 19 can display the processed results.

In the particle size distribution measuring apparatus constructed as described above, where the sample solution 2 is contained in the cell 1 and the laser beam is irradiated from the laser light source 3, the laser beam is converged by means of the condenser lens 4 so as to be made into a converged laser beam 5, and then, the converged laser beam 5 is irradiated to the sample solution 2 in the cell 1. Then, the converged laser beam 5 is diffracted or scattered by particles contained in the cell 1. Of the diffraction light or the scattering light, a light having a relatively small scattering angle is imaged on the ring detector 6. In this case, the photo-sensor arranged on the outer peripheral side of the ring detector 6 receives a light having a larger scattering angle; on the other hand, the photo-sensor arranged on the inner peripheral side thereof receives a light having a smaller scattering angle. Thus, a light intensity detected by the outer peripheral side photo-sensor represents a particle quantity having a smaller particle size, and a light intensity detected by the inner peripheral side photo-sensor represents a quantity of sample particle having a larger particle size. The light intensity detected by each photo-sensor is converted into an analog electric signal, and further, is inputted to the multiplexor 16 via the pre-amplifier 7.

On the other hand, of the converged laser beam 5 diffracted or scattered by the particles, a relatively large scattering angle light is detected by means of the optical detector group 8 for wide-angle scattering light, and then, the light intensity distribution is measured. In this case, the photo-sensors 9 to 12 for forward scattering light, the photo-sensor 13 for side scattering light and the photo-sensor 14 for backward scattering light, in this order, successively detects a scattering light from a particle having a small particle (grain) size. A light intensity detected by each of these photo-sensors 9 to 14 is converted into an analog electric signal, and then, is inputted to the multiplexor 16 via pre-amplifiers located on the electric circuit board 15.

In the multiplexor 16, measurement data from the ring detector 6 and photo-sensors 9 to 14, that is, the analog electric signal is successively captured in the predetermined order. Then the analog electric signal captured by the multiplexor 16 is made into a serial signal, and is successively converted into a digital signal by means of the A/D converter 17, and further, is inputted to the computer 18.

The computer 18 processes light intensity data for each scattering angle obtained by each of the ring detector 6 and the photo-sensors 9 to 14 on the basis of a Fraunhofer diffraction theory and a Mie scattering theory.

As seen from the above description, in the particle size distribution measuring apparatus, the light intensity distribution of the scattering light having a large particle size range is measured by means of the ring detector 6 and the light intensity distribution of the wide-angle scattering light having a small particle size range is measured by means of the photo-sensors 9 to 14. Then, the outputs of the ring detector 6 and photo-sensors 9 to 14 are processed by means of the computer 18, so that a particle size distribution of the particle group can be collectively determined over a wide range from a relatively large particle size to a micro particle size.

In the above particle size distribution measuring apparatus, the collective lens 4 is interposed between the laser beam source 3 and the cell 1, and the laser beam 5, converged by the collective lens 4, is irradiated to the particle group. Thus, unlike the conventional case, it is possible to collect light having a small scattering angle generated in particles having a relatively large particle size onto the ring detector 6 without interposing the collective lens between the cell 1 and the ring detector 6. Further, it is possible to make shorter the optical path length from the laser beam source 3 to the ring detector 6 as compared with the case where a parallel beam is irradiated to the particle group in the cell. Furthermore, the collective lens is not interposed between the cell 1 and the ring detector 6, therefore, it is possible to sufficiently secure a desired optical path of the scattering light from cell 1 to the optical detector group 8 for wide-angle scattering light from cell 1 to the optical detector group 8 for wide-angle scattering light, and to arbitrarily arrange photo-sensors 9 to 14 on a position equivalent to a scattering angle. Therefore, it is possible to simplify the construction of a particle size distribution measuring apparatus, and to obtain a small-size and compact particle size distribution measuring apparatus.

Figure 2:
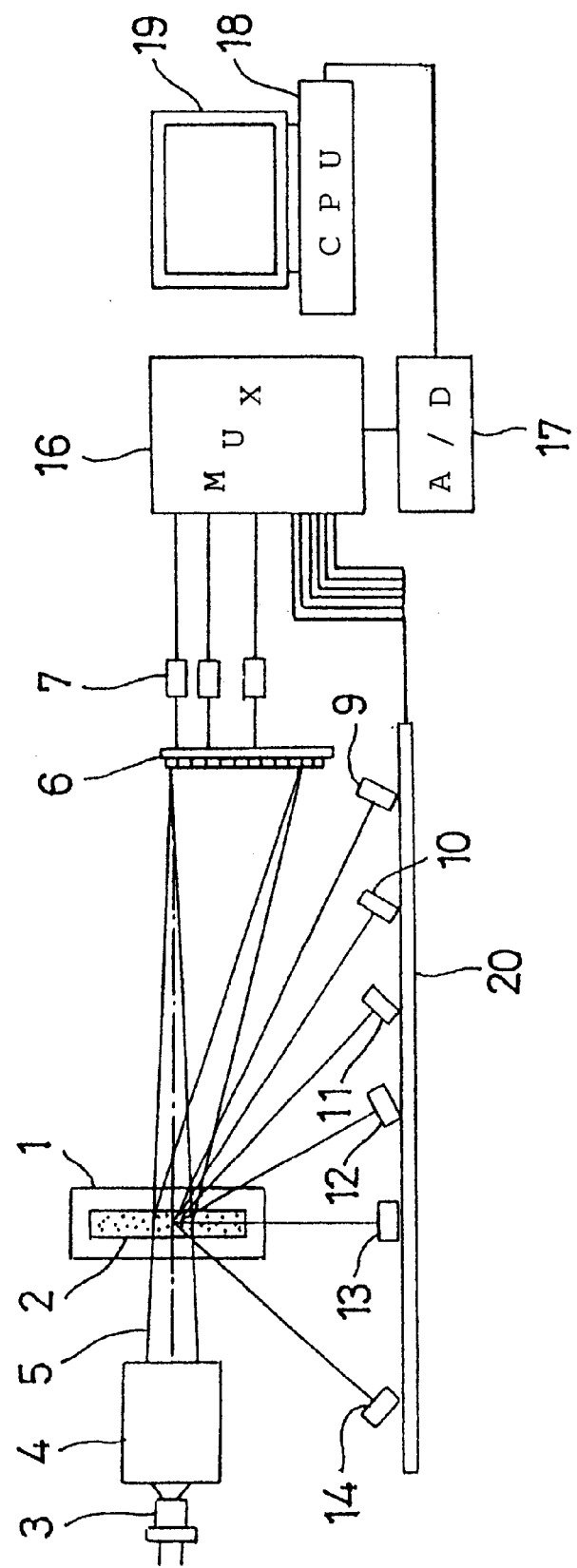
FIG. 2 is a view schematically showing a construction of a particle size distribution measuring apparatus according to a second embodiment of the present invention.

The present invention is not limited to the above embodiment, and various modifications can be carried out. More specifically, FIG. 2 shows a second schedule embodiment of the present invention with a quarter-ring detector 6. In this second embodiment, the photo-sensors 9 to 14 constituting the optical detector group for wide-angle scattering light can be arranged on a single substrate, such as an electric circuit board 20 with each sensor at a predetermined angle. Although it is not illustrated, a pre-amplifier is also located on the electric circuit board 20 so as to correspond to each of the photo-sensors 9 to 14. An output of the electric circuit board 20 is inputted to the multiplexor 16.

According to the above second embodiment, there is the following effect in addition to the effect of the aforesaid first embodiment. More specifically, there is no need of providing an electric circuit board 15 for each of the photo-sensors 9 to 14; therefore, a construction of an optical system becomes simple, and it is easy to construct and arrange the optical detector group 8 for wide-angle scattering light. As a result, it is possible to make the whole of the apparatus into a small size, and to achieve a reduction in both individual part cost and manufacture cost.

Figure 3:
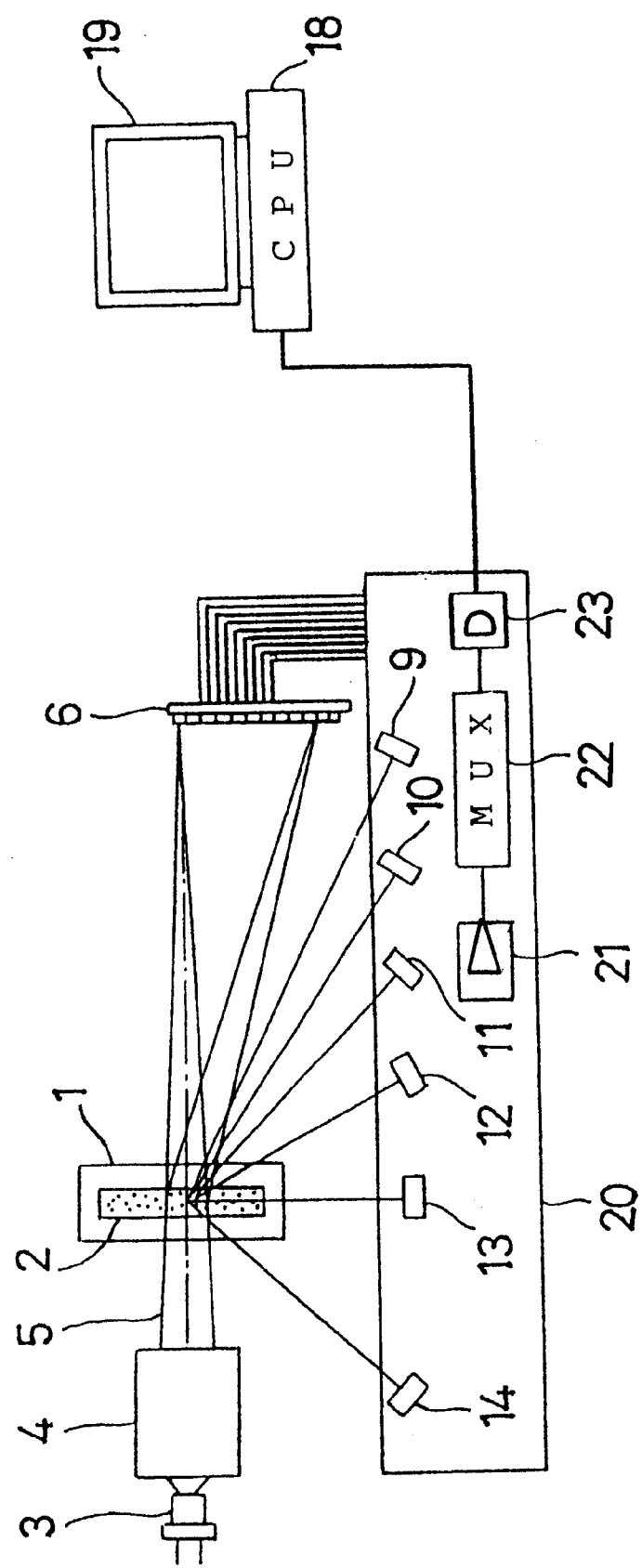
FIG. 3 is a view schematically showing a construction of a particle size distribution measuring apparatus according to a third embodiment of the present invention.
Figure 4:
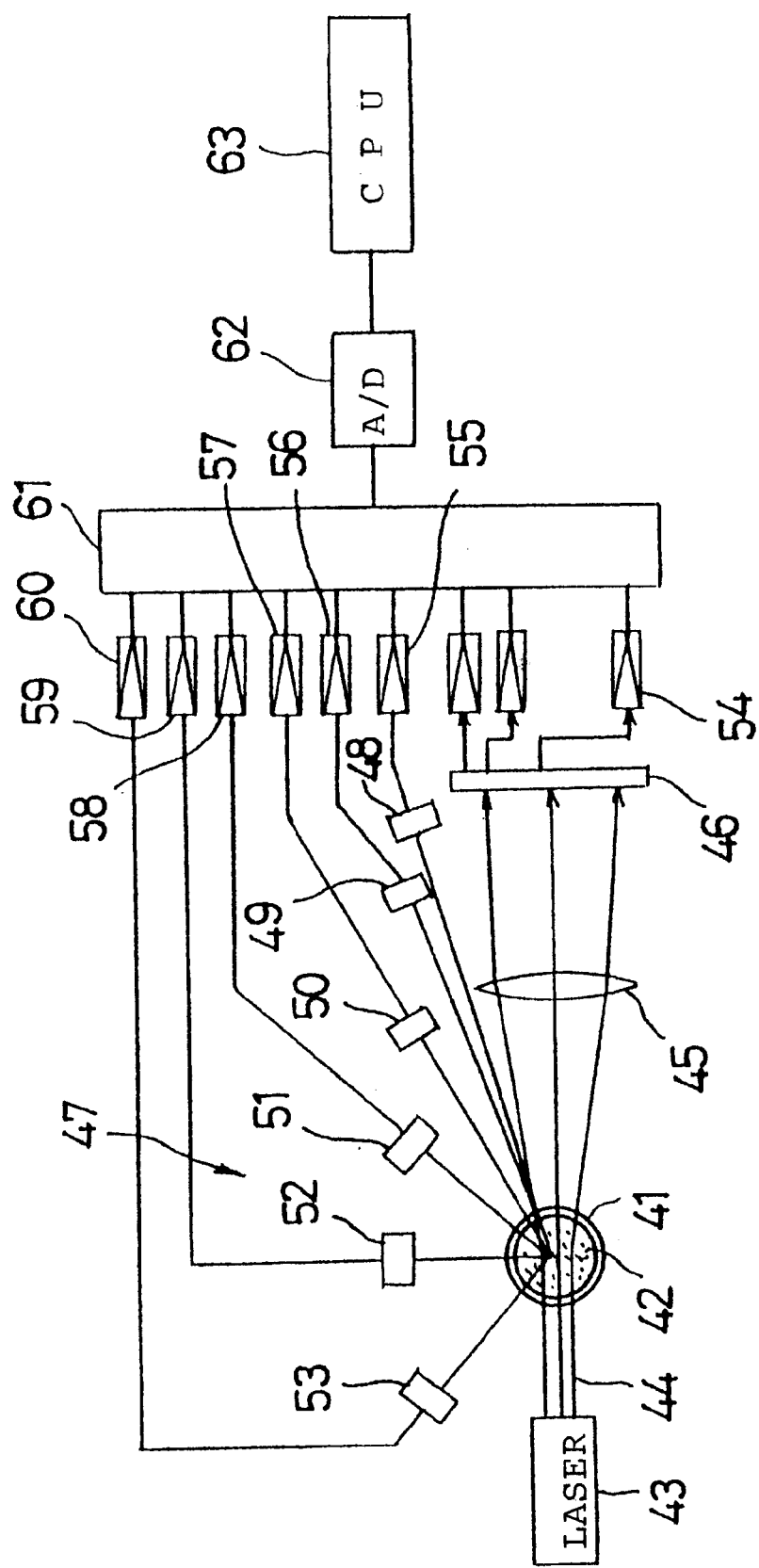
FIG. 4 is a view schematically showing a construction of a conventional particle size distribution measuring apparatus.

FIG. 3 shows a third embodiment of the present invention. In this third embodiment, the electric circuit board 20 is provided with a pre-amplifier section 21 which amplifies an output of each of the ring detector 6 and the photo-sensors 9 to 14, a multiplexor 22 which successively captures an output of the pre-amplifier 21 and outputs it to the computer 18, and an A/D converter 23 which converts an analog signal successively outputted from the multiplexor 22 into a digital signal. According to this third embodiment, there is the following effect in addition to the effect of the above second embodiment. More specifically, it is possible to provide a relatively short signal line from the photo-sensors 9 to 14, and to prevent noise from being mixed with the signals.

In the above embodiments, the sample solution 2 has been contained in the sample cell 1. The cell is not limited to the form described in the above embodiments, and a so-called flow cell where a stream of material flows pass the sampling site may be used. Moreover, as a target for measurement, in addition to particles in a liquid, a powder or particle dispersed in a gas or solid may be used.

In the present invention, the condenser lens is interposed between the laser light source and the sample cell, and a laser beam, converged by the condenser lens, is irradiated to the particle group. Thus, a light having a small scattering angle generated in the particles having a relatively large particle size can be converged onto the ring detector, and the optical path length from the laser beam source to the ring detector can be made short as compared with the case where a parallel laser beam is irradiated to the particle group in the cell. Further, there is no need of interposing the condenser lens between the cell and the ring detectors; therefore, it is possible to sufficiently secure a desirable optical path of the scattering light from the cell, and to selectively arrange the photo-sensor on a position equivalent to the scattering angle.

Accordingly, the construction of the particle size distribution measuring apparatus can be simplified to provide a small and compact size apparatus and it is possible to securely measure a particle size distribution of particles having a range from a micro particle size to a large particle size.

Those skilled in the art will appreciate that various adaptations and modifications of the just-described preferred embodiments can be configured without departing from the scope and spirit of the invention. Therefore, it is to be understood that within the scope of the appended claims, the invention may be practiced other than as specifically described herein.

What is claimed is:

1. A particle size distribution measuring apparatus comprising:
   a source of laser light for providing a laser beam;
   a sample cell for a sample to be measured;
   a condenser lens unit with a focal point positioned between the source of laser light and the sample cell for converging the laser beam toward the sample cell along an optical axis;
   a ring detector unit aligned with the optical axis on an opposite side of the sample cell from the source of laser light at the focal point of the condenser lens unit said ring detector having a plurality of discrete detection areas for measuring light intensity at relatively small scattering angles off of an optical axis of the laser beam;
   an array of detectors operatively positioned relative to the sample cell for measuring light intensity at relatively large scattering angles off of the optical axis; and
   means for determining the particle size distribution of particles in the sample based on outputs of the ring detector unit and the array of detectors.

2. A particle size distribution measuring apparatus of claim 1 wherein the ring detector unit has radially displaced detector channels and an outermost detector channel is aligned on the optical axis.

3. A particle size distribution measuring apparatus of claim 1 wherein the array of detectors is mounted on a single substrate.

4. A particle size distribution measuring apparatus of claim 3 wherein the single substrate is a printed circuit board and each individual detector forming the array is aligned at different angles to a plane containing a surface of the printed circuit board.

5. A particle size distribution measuring apparatus of claim 4 wherein a pre-amplifier is mounted on the printed circuit board for amplifying an output of an individual detector on the array.

6. A particle size distribution measuring apparatus of claim 5 wherein a multiplexor and A/D converter is mounted on the printed circuit board.

7. A particle size distribution measuring apparatus comprising:
- a source of laser light for providing a laser beam;
- a sample cell for a sample to be measured;
- a condenser lens unit with a focal point positioned between the source of laser light and the sample cell for converging the laser beam toward the sample cell along an optical axis;
- a ring detector unit aligned with the optical axis on an opposite side of the sample cell from the source of laser light at the focal point of the condenser lens unit; said ring detector having a plurality of discrete detection areas for measuring light intensity at relatively small scattering angles off of the optical axis;
- an array of detectors mounted on a printed circuit substrate and operatively positioned relative to the sample cell for measuring light intensity at relatively large scattering angles off of the optical axis;
- a plurality of detectors in the array positioned at different angles to a surface of the printed circuit substrate; and
- means for determining the particle size distribution of particles in the sample based on outputs of the ring detector unit and the array of detectors.

8. A particle size distribution measuring apparatus of claim 7 wherein the ring detector unit has radially displaced detector channels and an outermost detector channel is aligned on the optical axis.

9. The particle size distribution measuring apparatus of claim 7 wherein a pre-amplifier is mounted on the printed circuit substrate for amplifying an output of an individual detector on the array.

10. The particle size distribution measuring apparatus of claim 9, wherein a multiplexor and A/D converter is mounted on the printed circuit substrate.

11. The particle size distribution measuring apparatus of claim 7, wherein the differing angles of the plurality of detectors in the array incline from the surface of the printed circuit substrate.

12. The particle size distribution measuring apparatus of claim 7, wherein the differing angles of the plurality of detectors in the array decline from the surface of the printed circuit substrate.

13. A particle size distribution measuring apparatus comprising:
- a source of laser light for providing a laser beam;
- a sample cell for a sample to be measured;
- a condenser lens unit with a focal point positioned between the source of laser light and the sample cell for converging the laser beam toward the sample cell along an optical axis;
- a ring detector unit aligned with the optical axis on an opposite side of the sample cell from the source of laser light at the focal point of the condenser lens unit; said ring detector having a plurality of discrete detection areas for measuring light intensity at relatively small scattering angles off of an optical axis of the laser beam;
- a large angle detector array consisting of a plurality of detectors mounted on a single printed circuit substrate having a pre-amplifier for amplifying an output of an individual detector on the array; said large angle detector array operatively positioned relative to the sample cell for measuring light intensity at relatively large scattering angles off of the optical axis, said plurality of detectors in the large angle detector array positioned at different angles to a surface of the printed circuit substrate; and
- means for determining the particle size distribution of particles in the sample based on outputs of the ring detector unit and the array of detectors.

14. The particle size distribution measuring apparatus of claim 13, wherein the differing angles of the plurality of detectors in the array incline from the surface of the printed circuit substrate.

15. The particle size distribution measuring apparatus of claim 13, wherein the differing angles of the plurality of detectors in the array decline from the surface of the printed circuit substrate.

16. A particle size distribution measuring apparatus comprising:
- a source of laser light for providing a laser beam;
- a sample cell for a sample to be measured;
- a condenser lens unit positioned between the source of laser light and the sample cell for converging the laser beam toward the sample cell along an optical axis;
- a ring detector unit aligned with the optical axis on an opposite side of the sample cell from the source of laser light without a lens placed between the sample cell and the ring detector unit; said ring detector having a plurality of discrete detection areas for measuring light intensity at relatively small scattering angles off of an optical axis of the laser beam;
- an array of detectors operatively positioned relative to the sample cell for measuring light intensity at relatively large scattering angles off of the optical axis; and
- means for determining the particle size distribution of particles in the sample based on outputs of the ring detector unit and the array of detectors.

17. The particle size distribution measuring apparatus of claim 16 where the ring detector unit is a quarter ring detector.

* * * * *